United States Patent
Mault

(10) Patent No.: US 6,572,561 B2
(45) Date of Patent: Jun. 3, 2003

(54) RESPIRATORY CALORIMETER

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 0 days.

(21) Appl. No.: 10/096,202

(22) Filed: Mar. 12, 2002

(65) Prior Publication Data

US 2002/0173728 A1 Nov. 21, 2002

Related U.S. Application Data

(63) Continuation-in-part of application No. 10/057,651, filed on Oct. 29, 2001, which is a continuation of application No. 09/008,435, filed on Jan. 16, 1998, now Pat. No. 6,309,360.

(51) Int. Cl.$^7$ .................................................. A61B 5/08
(52) U.S. Cl. ...................... 600/532; 600/538; 600/529; 600/531
(58) Field of Search ................................. 600/529, 531, 600/532, 538; 128/200.24

(56) References Cited

U.S. PATENT DOCUMENTS

| | | | |
|---|---|---|---|
| 2,826,912 A | 3/1958 | Kritz | 73/194 |
| 2,831,348 A | 4/1958 | Kritz | 73/861.28 |
| 2,869,357 A | 11/1959 | Kritz | 73/32 |
| 2,911,825 A | 11/1959 | Kritz | 73/194 |
| 3,220,255 A | 11/1965 | Scranton et al. | 73/204 |
| 3,962,917 A | 6/1976 | Terada | 73/204 |
| 4,078,554 A | 3/1978 | Lemaitre et al. | 128/2.08 |
| 4,197,857 A | 4/1980 | Osborn | 600/531 |
| 4,233,842 A | * 11/1980 | Raemer et al. | 73/861.04 |
| 4,368,740 A | * 1/1983 | Binder | 600/531 |
| 4,425,805 A | 1/1984 | Ogura et al. | 73/861.29 |
| 4,440,177 A | 4/1984 | Anderson et al. | 600/532 |
| 4,463,764 A | 8/1984 | Anderson et al. | 600/532 |
| 4,648,396 A | 3/1987 | Raemer | 600/534 |
| 4,658,832 A | 4/1987 | Brugnoli | 600/532 |
| 4,796,639 A | 1/1989 | Snow et al. | 600/532 |
| 4,850,371 A | 7/1989 | Broadhurst et al. | 600/532 |
| 4,856,531 A | 8/1989 | Merilainen | 600/532 |
| 4,859,858 A | 8/1989 | Knodle et al. | 250/504 |
| 4,859,859 A | 8/1989 | Knodle et al. | 250/504 |
| 4,909,259 A | 3/1990 | Tehrani | 600/531 |
| 4,914,720 A | 4/1990 | Knodle et al. | 250/343 |
| 4,914,959 A | 4/1990 | Mylvaganam et al. | 73/861.28 |
| 4,917,108 A | 4/1990 | Mault | 65/273 |
| 4,955,946 A | 9/1990 | Mount et al. | 600/532 |
| 4,958,075 A | 9/1990 | Mace et al. | 250/343 |
| 4,986,268 A | 1/1991 | Tehrani | 128/204 |
| 4,998,018 A | 3/1991 | Kurahashi et al. | 250/343 |

(List continued on next page.)

Primary Examiner—Max F. Hindenburg
Assistant Examiner—Navin Natnithithadha
(74) Attorney, Agent, or Firm—Gifford, Krass, Groh, Sprinkle, Anderson & Citkowski, P.C.

(57) ABSTRACT

An indirect calorimeter operative to measure the respiratory oxygen consumption per unit time of a subject includes a respiratory connector operative to be supported in contact with a subject, so as to pass respiratory gases as the subject breathes into the respiratory connector, and a bi-directional flow meter having an ultrasonic flow transducer that bi-directionally transmits and receives ultrasonic signals to the transducer to generate a signal as a function of the volume of gases passing through the flow meter. The indirect calorimeter also includes a gas concentration sensor operative to generate a signal as a function of an instantaneous carbon dioxide content of gases passing by the gas concentration sensor. The indirect calorimeter further includes a computing device operative to receive signals from the flow meter and the gas concentration sensor, and conduits interconnecting the respiratory connector, the flow meter and the gas concentration sensor, so that the subject's inhalations and exhalations pass through the flow meter and the subject's exhalations pass over the gas concentration sensor and the computer is operative to receive the signals from the gas concentration sensor and the flow meter to calculate the subject's oxygen consumption.

22 Claims, 2 Drawing Sheets

U.S. PATENT DOCUMENTS

| | | | |
|---|---|---|---|
| 5,038,773 A | 8/1991 | Norlien et al. | 128/205.23 |
| 5,038,792 A | 8/1991 | Mault | 128/718 |
| 5,042,500 A | 8/1991 | Norlien et al. | 600/532 |
| 5,042,501 A | 8/1991 | Kenny et al. | 600/532 |
| 5,060,506 A | 10/1991 | Douglas | 73/24.1 |
| 5,060,655 A | 10/1991 | Rudolph | 128/716 |
| 5,081,871 A | 1/1992 | Glaser | 73/863.23 |
| 5,095,900 A | 3/1992 | Fertig et al. | 128/704.14 |
| 5,117,674 A | 6/1992 | Howard | 73/31.07 |
| 5,119,825 A | 6/1992 | Huhn | 600/529 |
| 5,178,155 A | 1/1993 | Mault | 128/718 |
| 5,179,958 A | 1/1993 | Mault | 128/718 |
| 5,214,966 A | 6/1993 | Delsing | 73/861.28 |
| 5,233,996 A | 8/1993 | Coleman et al. | 600/529 |
| 5,282,473 A | 2/1994 | Braig et al. | 600/532 |
| 5,299,579 A | 4/1994 | Gedeon et al. | 600/532 |
| 5,303,712 A | 4/1994 | Van Duren | 600/529 |
| 5,309,921 A | 5/1994 | Kisner et al. | 600/532 |
| 5,326,973 A | 7/1994 | Eckerbom et al. | 250/343 |
| 5,357,972 A | 10/1994 | Norlien | 128/725 |
| 5,363,857 A | 11/1994 | Howard | 600/531 |
| 5,398,695 A | 3/1995 | Anderson et al. | 600/532 |
| 5,419,326 A | 5/1995 | Harnoncourt | 128/660.02 |
| 5,425,374 A | 6/1995 | Ueda et al. | 600/532 |
| 5,450,193 A | 9/1995 | Carlsen et al. | 356/301 |
| 5,503,151 A | 4/1996 | Harnoncourt et al. | 128/660.02 |
| 5,517,313 A | 5/1996 | Colvin, Jr. | 356/417 |
| 5,645,071 A | 7/1997 | Harnoncourt et al. | 128/719 |
| 5,647,370 A | 7/1997 | Harnoncourt | 128/725 |
| 5,676,132 A | 10/1997 | Tillotson et al. | 128/204.23 |
| 5,705,735 A | 1/1998 | Acorn | 73/23.3 |
| 5,743,253 A | 4/1998 | Castor et al. | 128/200 |
| 5,754,288 A | 5/1998 | Yamamoto et al. | 356/301 |
| 5,789,660 A | 8/1998 | Kofoed et al. | 73/232 |
| 5,796,009 A | 8/1998 | Delsing | 73/861.28 |
| 5,800,360 A | 9/1998 | Kisner et al. | 600/532 |
| 5,816,246 A | 10/1998 | Mirza | 128/726 |
| 5,831,175 A | 11/1998 | Fletcher-Haynes | 73/861.28 |
| 5,834,626 A | 11/1998 | DeCastro et al. | 73/23.3 |
| 5,836,300 A | 11/1998 | Mault | 128/204.23 |
| 5,894,351 A | 4/1999 | Colvin, Jr. | 356/417 |
| 5,910,661 A | 6/1999 | Colvin, Jr. | 250/573 |
| 5,917,605 A | 6/1999 | Colvin, Jr. | 356/417 |
| 5,922,610 A | 7/1999 | Alving et al. | 436/116 |
| 5,932,812 A | 8/1999 | Delsing | 73/861.02 |
| 5,957,858 A | 9/1999 | Micheels et al. | 600/532 |
| 6,010,459 A | 1/2000 | Silkoff et al. | 600/532 |
| 6,044,843 A | 4/2000 | O'Neil et al. | 128/204.23 |
| 6,135,107 A | 10/2000 | Mault | 128/204.23 |
| 6,277,645 B1 | 8/2001 | Mault | 436/133 |
| 6,309,360 B1 | 10/2001 | Mault | 600/531 |

\* cited by examiner

RESPIRATORY CALORIMETER

RELATED APPLICATIONS

This application is a continuation-in-part of U.S. patent application Ser. No. 10/057,651, filed Oct. 29, 2001, which is a continuation of Ser. No. 09/008,435 filed Jan. 16, 1998 U.S. Pat. No. 6,309,360 B1.

FIELD OF THE INVENTION

This invention relates to indirect calorimeters for determining the metabolic rates of subjects by measuring their oxygen consumption during respiration over a period of time, and more particularly to such a calorimeter employing the utility of a flow meter and a component gas concentration sensing device.

BACKGROUND OF THE INVENTION

Measurement of the energy expenditure of humans is important for a number of reasons, including the determination of the proper caloric content for feedings of hospitalized patients whose metabolisms may deviate from normal values, the monitoring of progress of weight loss diets to allow the adjustment of caloric inputs to achieve a target loss and the determination of energy expenditure during exercise.

A variety of indirect calorimeters for measuring oxygen consumption during respiration have been devised. One form of respiratory calorimeter, disclosed in U.S. Pat. Nos. 4,917,108; 5,038,792; 5,179,985 and 5,178,155, all to Mault, measures the volume of a subject's inhalations over a period of time, and the volume of the subject's exhalations after carbon dioxide in the exhalations has been removed by an absorbent scrubber. These measurements are integrated over the time of measurement and the difference between the two summed volumes is a measure of the subject's oxygen consumption. This follows from the fact that inhaled oxygen is either absorbed into the blood in the subject's lungs or expelled during exhalation. Some portion of the blood absorbed oxygen is replaced with $CO_2$. When the $CO_2$ is removed from the exhaled volume, the summed difference between inhalation and exhalation volume over a period of time is equal to the absorbed oxygen.

In some versions of these prior calorimeters, a capnometer was also used to measure the instantaneous value of the exhaled $CO_2$ in a breath allowing the calculation of $CO_2$ production, Resting Energy Expenditure (REE) and Respiratory Quotient (RQ).

An absorbent scrubber used with these previous systems, such as sodium hydroxide or calcium hydroxide, which reacts with the $CO_2$ to form water plus a salt, has a limited ability to absorb $CO_2$ and must be replenished after a period of use. The scrubber is also large and heavy relative to the other components of the calorimeter. Thus, there is a need in the art for an indirect calorimeter that utilizes a component gas concentration sensor in place of a scrubber to determine the volume of exhaled carbon dioxide.

SUMMARY OF THE PRESENT INVENTION

The present invention is an indirect calorimeter operative to measure the respiratory oxygen consumption per unit time of a subject. The indirect calorimeter includes a respiratory connector operative to be supported in contact with a subject, so as to pass respiratory gases as the subject breathes into the respiratory connector and a bi-directional flow meter having an ultrasonic flow transducer that bi-directionally transmits and receives ultrasonic signals to the transducer to generate a signal as a function of the volume of gases passing through the flow meter. The indirect calorimeter also includes a gas concentration sensor operative to generate a signal as a function of an instantaneous carbon dioxide content of gases passing by the gas concentration sensor. The indirect calorimeter further includes a computer operative to receive signals from the flow meter and the gas concentration sensor, and conduits interconnecting the respiratory connector, the flow meter and the gas concentration sensor, so that the subject's inhalations and exhalations pass through the flow meter and the subject's exhalations pass over the gas concentration sensor and the computer is operative to receive the signals from the gas concentration sensor and the flow meter to calculate the subject's oxygen consumption.

One advantage of the present invention is that the need for the carbon dioxide scrubber is eliminated by measuring the volume of exhaled carbon dioxide and subtracting that volume from the total exhaled volume over the measurement period to calculate a summed difference that is then subtracted from the inhaled volume to arrive at $VO_2$ consumed. Another advantage of the present invention is that the volume of exhaled carbon dioxide is determined by integrating the instantaneous carbon dioxide percentage of the exhalation, as measured by a component gas concentration sensing device, over the exhaled volume as measured by a flow meter: $VCO_2 = V_e(\% CO_2)$.

The flow meter generates an electrical signal as a function of the instantaneous flow volume and this signal is preferably sent to a microprocessor-based computer along with the electrical output of a capnometer sensor. Still another advantage of the present invention is that the gas concentration sensing device generates electrical output signals representative of certain gaseous percentages, namely $O_2$ and/or $CO_2$, in the inhaled and exhaled flow volume and these signals are sent to the microprocessor-based computer along with the signal from the flow meter. Still yet another advantage of the present invention is that a bi-directional flow meter is used to measure both the inhaled and exhaled flow volume. A temperature and/or humidity conditioner may be utilized to equalize the temperature and/or humidity of the incoming air to that of the exhaled air, so that uniform flow measurements may be made. Alternatively, the system could receive signals representing temperature, humidity and/or barometric pressure from sensors disposed in the calorimeter or externally, or keyboard entries and calculate correction factors for the flow measurement based on the signals. A further advantage of the present invention is that the distinction between inhalations and exhalations is determined by the presence or absence of $CO_2$ in the flowing gas as measured by the component gas concentration sensing device, such as an infrared absorption sensor, that determines the amount of a particular gas in a volume of inhaled or exhaled air and outputs an electrical signal representative of the measured amount.

Yet a further advantage of the present invention is that the microprocessor, in addition to calculating and displaying the $VO_2$, is used to calculate and display REE, RQ and the rate of carbon dioxide production.

Still yet a further advantage of the present invention is that the subject's Cardiac Output is calculated using a noninvasive method of cardiac output measurement using partial $CO_2$ rebreathing described in an article by Capek and Roy in *IEEE Transactions and Biomedical Engineering*, Vol. 35, pages 653–61, 1988. This embodiment of the invention employs a two stage measurement. In the first stage, the device is configured in essentially the same manner as the other embodiments of the invention to measure oxygen consumption. Over a period of use, such as three minutes, the microprocessor measures $VO_2$, $VCO_2$, and the end-tidal $CO_2$ ($etCO_2$) which is the carbon dioxide content of a breath at the end of an exhalation. These values are stored and the device is then switched to a configuration in which the end portion of each exhalation is not expelled from the device, but is rather captured, so that it forms the initial portion of the gas provided to the subject during the next inhalation. This is achieved by creating a dead space chamber in the exhalation passage. The subject breathes in this manner for a short period such as 30 seconds. During this period the breath-to-breath $etCO_2$ and the total $VCO_2$ are recorded. The computer then implements the calculation:

$$C.O. = \frac{\Delta VCO_2}{\Delta etCO_2}$$

where $\Delta VCO_2$ equals the difference in the total volume of exhaled $CO_2$, per breath, during the two recordings and $\Delta etCO_2$ is the difference in the end-tidal $CO_2$ between the two recordings.

Other features and advantages of the present invention will be readily appreciated, as the same becomes better understood after reading the subsequent description taken in conjunction with the accompanying drawings.

DETAILED DESCRIPTION OF THE INVENTION

Figure 1:
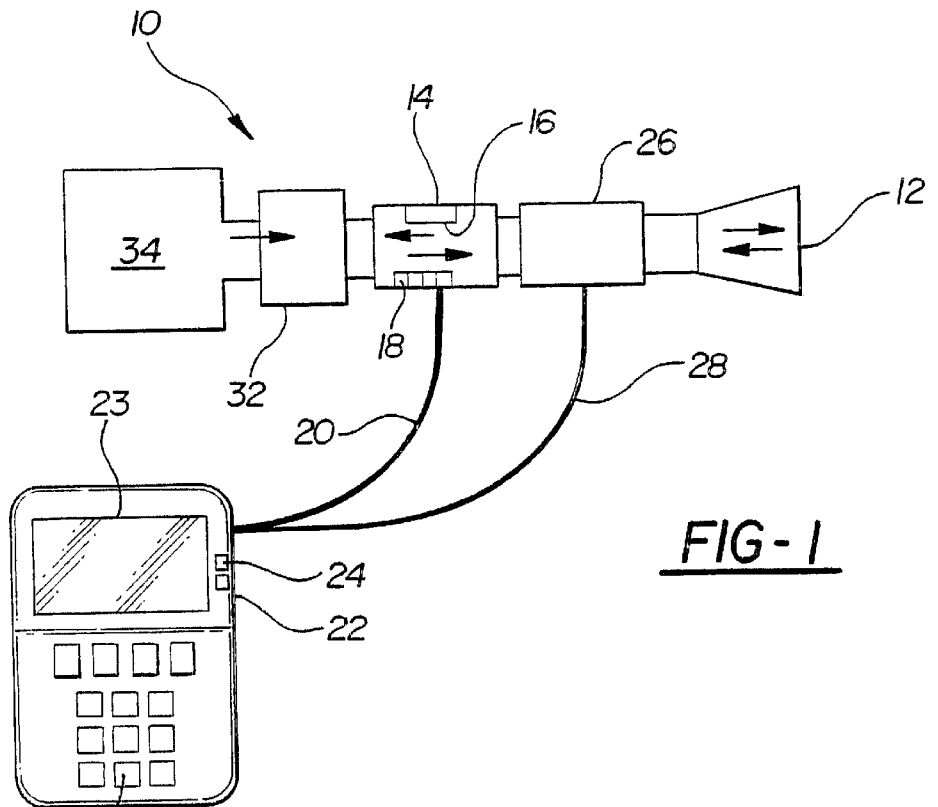
FIG. 1 is a schematic diagram of a preferred embodiment of a respiratory calorimeter employing a bi-directional flow meter and a component gas concentration sensor providing electrical outputs to a microprocessor-based computer.

Referring to FIG. 1, which schematically illustrates a preferred embodiment of the present oxygen consumption meter 10, a source of respiratory gases, which may be ambient air or some form of positive-pressure ventilator is schematically illustrated at 34. A subject or patient whose respiratory function is being measured breathes through a respiratory connector taking the form of a mouthpiece 12 adapted to engage the inner surfaces of the user's mouth, so as to form the sole passage for inhaled and exhaled air passing through the mouth. A nose clamp (not shown) of conventional construction may be employed to assure that all the respiratory air passes through the mouthpiece 12. In alternative configurations, a mask that engages the nose as well as the mouth might be employed.

The system 10 includes a bi-directional flow meter 14. One example of a bi-directional flow meter is a pressure differential flow meter having pressure differential transducers, such as that manufactured by Medical Graphics Corporation of St. Paul, Minn. under the trademark "MEDGRAPHICS". Another example of a flow meter is a differential temperature flow meter. Still another example of a flow meter is an ultrasonic flow meter.

The ultrasonic flow meter 14 includes an ultrasonic flow transducer 16 that is used in combination with an application specific integrated circuit (ASIC), that all form part of the ultrasonic flow sensing system. Preferably, the ultrasonic transducer 16 is strategically placed within the upper and lower wall of flow meter 14 to bi-directionally transmit and receive ultrasonic signals. It should be appreciated that an example of measurement of flow velocity using ultrasonic pulses is described in U.S. Pat. Nos. 5,419,326; 5,503,151; 5,645,071; and 5,647,370, all to Harnoncourt et al, which are incorporated herein by reference. In the Harnoncourt patents, ultrasonic transducers are positioned so as to transmit pulses through a flowing fluid in a direction that has a component in the flow direction. Specifically, with fluid flowing through a tube, the transducers are positioned in the side walls of the tube at an angle, such that ultrasonic pulses are transmitted at an angle to the fluid flow. Flow speed may be calculated based on the fact that components of the ultrasonic pulses traveling with the flow travel faster, while those components of the ultrasonic pulses traveling against the flow travel slower. Mathematical corrections are made for the fact that the ultrasonic pulses are traveling at an acute angle to the gas flow direction. Preferably, pulses are alternately transmitted in a direction with the flow and in a direction against the flow, and a time difference is calculated.

One example of an ultrasonic flow meter 14 is supplied by NDD of Zurich, Switzerland and Chelmsford, Mass. This ultrasonic flow meter 14 includes a micro-machined ultrasonic transducer array as shown at 18, which is available from Sensant of San Jose, Calif. This ultrasonic transducer includes a metalized polymer film and a perforated metal sheet. These sensors have the advantage of low noise, high frequency range, and potentially lower drive voltages. For example, pulse repetition rates may be higher, allowing instantaneous flow rates to be measured more frequently (i.e. with higher resolution), giving more accurate integrated flow volumes. Micro-machined temperature, pressure, and humidity sensors may be integrated into the ultrasonic arrays, to provide compensation for the effects of these environmental factors on the performance of the ultrasonic transducer. For example, distortion of micro-machined structures due to environmental effects is monitored using electric capacitance. Using an array, or a number of arrays, transit time variation over the lateral dimension perpendicular to flow direction) of the flow tube is measured (cross-sectional flow imaging) and integrated. Different sensors on the array are used as transmitters and detectors at the same time, bi-directional transit times are measured simultaneously, so that averaging methods are not required.

As will be clear to those of skill in the art, other approaches to flow sensing may also be used in place of, or in addition to, the ultrasonic flow meter of the present invention. Other examples of flow sensors include tiny impellers in the flow path, a hot wire based mass flow meter, and a pressure differential flow meter.

It should be appreciated that if the gas flow rate is zero, the transit times in either direction through the gas are the same, since both are related to the speed of sound and distance traveled. However, if the gas flow rate is not zero, the transit times differ between one direction and the other. For constant flow, the difference between bi-directional transit times is directly related to the gas flow speed. The ultrasonic transducers 16 are preferably controlled by an ASIC (application-specific integrated circuit), using transducer control circuitry. The ASIC is used to control the transmission and detection of ultrasonic pulses, and communicates with the CPU in the microprocessor based computer.

The flow meter 14 is designed to accurately measure gases flowing from the device in either direction. In a preferred embodiment, two separate tubular lines 20 interconnect the flow meter 14 with a pair of pressure transducers 24 disposed within a microprocessor-based computation and display device 22 having a display 23.

One end of the flow meter 14 is connected to a component gas concentration sensor 26. One example of a component gas concentration sensing device is a capnometer. Another example is a fluorescence quench sensor or an infrared absorption sensor. Preferably, the capnometer is operative to generate an electrical signal which is a function of the percentage of $CO_2$ concentration in the exhalation gas volume passing therethrough. The capnometer may be of a conventional type such as those described in U.S. Pat. No. 4,859,858; 4,859,859; 4,914,720; or 4,958,075. The electrical signal from the capnometer is provided to the microprocessor-based computer 22 over line 28. Novametrix Medical Systems Inc. of Wallingford, Conn. manufactures a respiratory profile monitor employing a combined capnometer and flow meter which could be used with the present invention.

Another example of a component gas concentration sensor 26 is an infrared absorption sensor that measures the amount of carbon dioxide present in the exhaled gas volume. Similar to the capnometer, the infrared sensor generates an electrical output signal representative of the $CO_2$ concentration in a respiratory exhalation and the signal is provided to the computing device 22 over line 28. Gas concentration is measurable using a variety of techniques.

Still another example of a component gas concentration sensor 26 is an IR absorption carbon dioxide sensor or fluorescence based oxygen sensors that are known in the art as component gas sensing devices. An example of an IR absorption carbon dioxide sensor or fluorescence based oxygen sensor is as disclosed by Colvin (U.S. Pat. Nos. 5,517,313; 5,894,351; 5,910,661; and 5,917,605; and PCT International Publication WO 00/13003, all of which are incorporated herein by reference). The IR absorption carbon dioxide sensor or fluorescence based oxygen sensor typically includes a permeable film in which component gas-indicating molecules are embedded. The component gas diffuses into the permeable film from the gas flowing over the film, inducing a chemical reaction. Preferably, an LED and a photodiode are mounted in general proximity to the component gas sensor for the purpose of exciting and measuring fluorescence in the sensor, respectively. Preferably, optical filters are employed in the system so that a common LED and photodiode may be used for sensing oxygen and carbon dioxide.

Referring back to FIG. 1, the other end of flow meter 14 is connected to a temperature and/or humidity conditioner unit 32. This unit acts to operate upon inhaled respiratory gases to bring either or both their moisture content or temperature into close alignment with the exhaled gases to improve the accuracy of the flow measurement made by the meter 14. The humidity conditioning function may be provided by a moisture absorbing filter such as a filter formed of fiber cellular material or a sponge, of the type termed a "artificial nose". This unit acts to absorb water vapor from gases passing through it if the water vapor content of the gases is higher than the level of moisture contained in the filter or to add water vapor to the gases if the filter vapor level is higher than that of the gases. Since the unit 32 passes both the inhaled gases and the exhaled gases, it tends to equalize them. The unit might also incorporate an active heating element to bring cooler gases from the respiratory source up to the body temperature of the exhalations.

Alternatively, the system 10 receives signals representing barometric pressure, room temperature, and humidity from sensors or keyboard entries and calculate correction factors for the flow measurement based on these signals. The distinction between inhalations and exhalations is determined by the presence or absence of $CO_2$ in the flowing gas as measured by the component gas concentration sensor 26 or in combination with analysis of the flow meter signal by a zero crossing algorithm. For example, carbon dioxide is measured using an IR absorption sensor and analyzed using the strong carbonyl absorption, or other such analytical techniques, such as those listed above for oxygen. It should be appreciated that carbon dioxide and oxygen sensors may be packaged together as a combined IR absorption/fluorescent quenching sensor, for example, using selectively permeable membranes or different fluorescent compounds.

The other end of the conditioner unit 32 is connected to the respiratory gas source 34. Accordingly, upon the subject inhaling, gas is drawn through the chain of the temperature/humidity compensator 32, the capnometer 26 and the flow meter 14 from the source of respiratory gases 34. Exhalations pass through the chain of elements 32, 26 and 14 in the reverse direction.

The microprocessor-based computation and display device 22 receives the two pressure signals from the flow meter via line 20 and from the capnometer via line 28. During a test, typically lasting 3–5 minutes, the microprocessor-based computer 22 integrates the signals from the flow meter 14 during inhalations and similarly integrates the flow meter readings during exhalations. The computing device 22 may also generate a signal representative of the total volume of $CO_2$ exhaled during the test period by multiplying the percentage $CO_2$ signal on line 28 with the volume signal on line 20 and integrating the value over the test. The computing device 22 can then calculate and display the oxygen consumption per unit time $VO_2$ on the display 23 by subtracting the exhaled $CO_2$ volume from the total exhaled volume and subtracting their difference from the inhaled volume. It can also display the exhaled $CO_2$ volume on the display 23 of the display device 22. The computer 22 preferably operates on a digital basis and if the signals on lines 20 and 28 are analog signals, as they are in the preferred embodiment of the invention, it digitizes those signals. A keyboard 42 associated with the computing device 22 allows for the user input of various factors as is understood in the art.

In addition to calculating the oxygen consumption of the subject, $VO_2$, and the resting energy expenditure in kilocalories per unit time, the computer 22 preferably generates a display of the exhaled $CO_2$ volume per unit time, RQ, which equals $VCO_2/VO_2$ and REE preferably calculated from the Weir equation: REE(KC/24 hours)=1440($VO_2 \times 3.341$)+($VCO_2 \times 1.11$) where $VO_2$ and $VCO_2$ are both measured in milliliters per minute.

Figure 2:
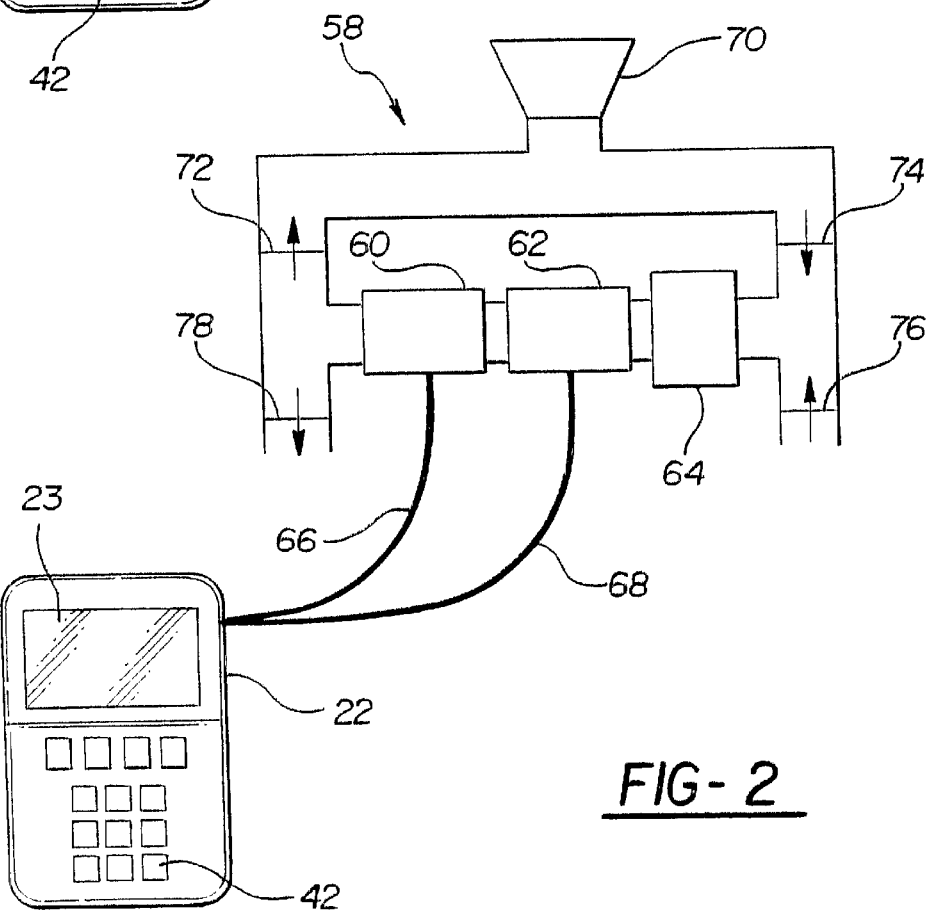
FIG. 2 is a schematic diagram of a respiratory calorimeter representing another embodiment of the present invention utilizing a unidirectional flow meter and conduits and valvings which direct the subject's inhalations and exhalations through the flow meter in the same direction.

Another embodiment of the calorimeter 58, illustrated in FIG. 2, employs a unidirectional flow meter 60 connected by conduits between a capnometer sensor 62 and a temperature and/or humidity conditioner 64. It should be appreciated that like features have like reference numerals. The flow meter 60 provides a pair of pressure signals on line 66 to appropriate transducers disposed within a microprocessor-based computation and display device 22 having a keyboard 42 and a display 23. A component gas concentration sensing device, such as a capnometer 62, provides an electrical output signal on line 68 to the computer 22. A patient connection such as a mouthpiece 70 receives inhaled gas from the output of the flow meter 60 via a one-way valve 72. Exhalations through the mouthpiece 70 are passed by a one-way valve 74 to the inlet of the conditioner 64. The respiratory gas inlet to the device, from the ambient air or a ventilator, is through a one-way valve 76, and the outlet of the device back to that source is through a fourth one-way valve 78.

Upon the subject inhaling through the connector 70, respiratory gases are drawn in through the valve 76, pass through the series chain of the conditioner 64, capnometer 62 and flow meter 60, and are directed by the valve 72 to the mouthpiece 70. Upon exhalation the valve 72 blocks flow so that gases pass through the valve 74, through the chain 64, 62, and 60 in the same direction as the inhalation, and through the valve 78 to the source of respiratory gases since the exhalation pressure on the outlet side of valve 72 prevents flow in that direction.

In both of these embodiments it should be understood that the use of temperature and/or humidity conditioning is optional and if used is intended to improve the precision of the measurements.

Figure 3:
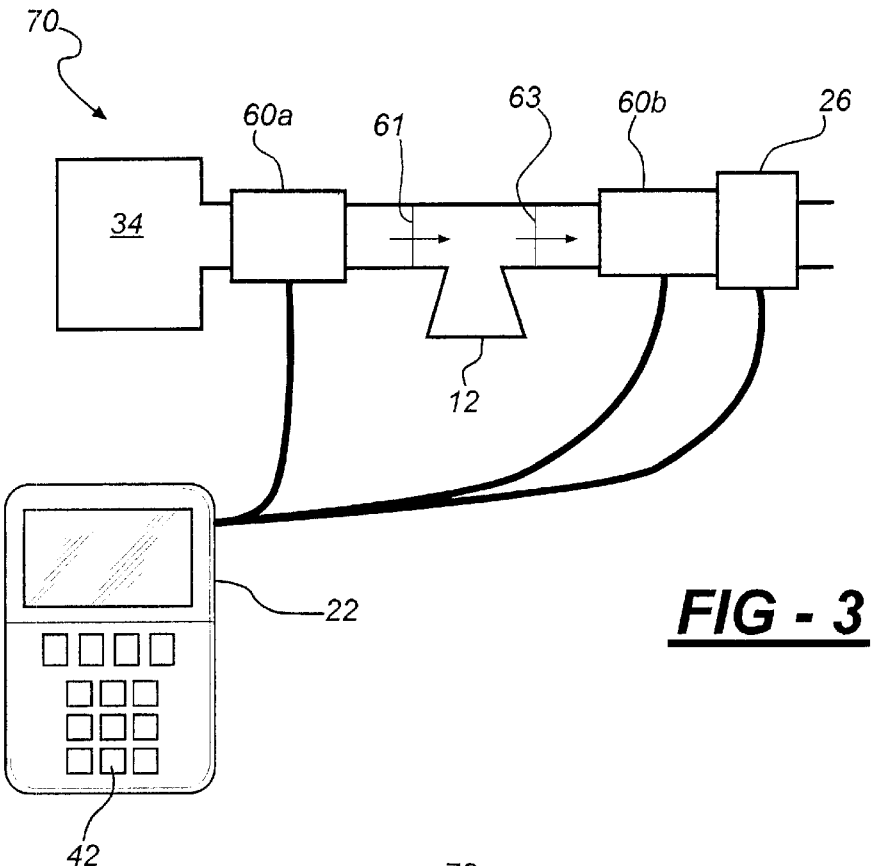
FIG. 3 is still another embodiment of the indirect calorimeter employing two unidirectional flow meters.

Still another embodiment of the invention, illustrated at 70 in FIG. 3, employs two unidirectional flow meters 60a and 60b, both connected to a microprocessor-based computation and display device 22. It should be appreciated that like features have like reference numerals. The outlet of flow meter 60a is connected to the mouthpiece 12 through a one-way valve 61 and the output of the mouthpiece 12 is connected to the inlet of the second flow meter 60b via a second one-way valve 63. The output of flow meter 60b passes through a capnometer 26 to the respiratory gas source 34. The capnometer is also connected to the computer. This embodiment is simple and provides the accuracy of unidirectional flow meters.

Figure 4:
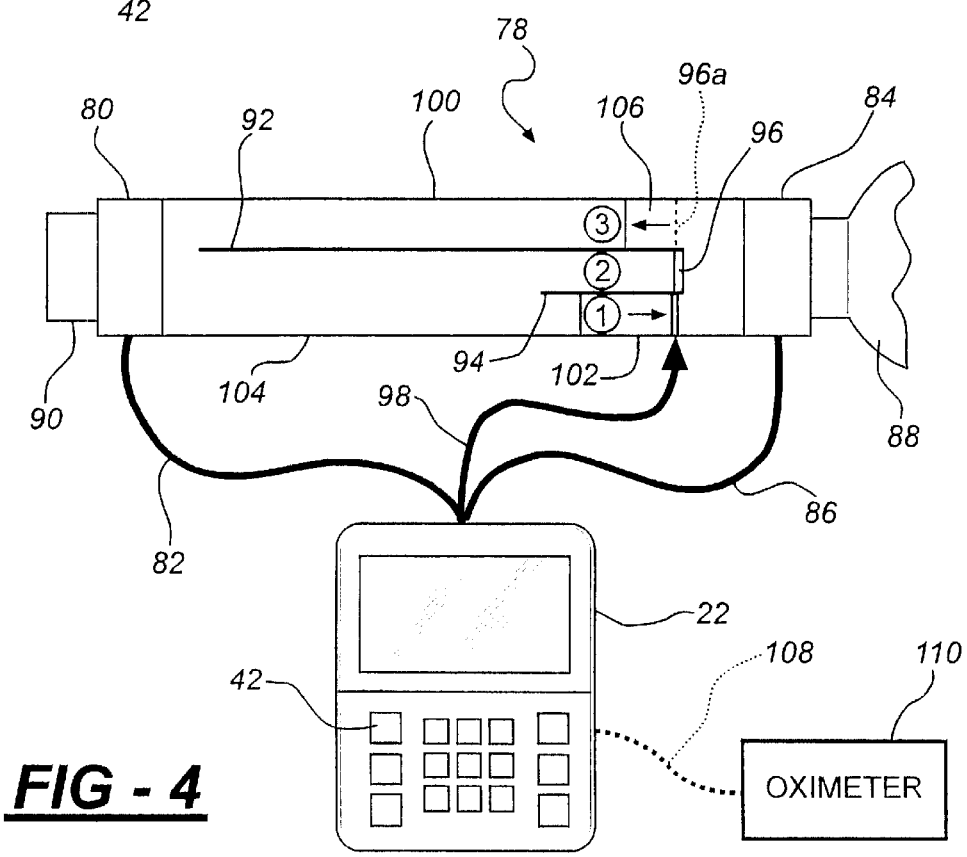
FIG. 4 is a schematic diagram of yet another embodiment of the invention constituting an oxygen consumption system and cardiac output measurement system.

A further embodiment of the invention illustrated at 78 in FIG. 4 allows the measurement of the subject's Cardiac Output (CO) as well as oxygen consumption and the other parameters measured by the previous embodiments of the invention. It should be appreciated that like features have like reference numerals. Like the embodiment of FIG. 1, the system of FIG. 4 employs a bi-directional volume flow meter 80 operative to provide pressure signals as a function of the instantaneous gas flow volume through it on line 82 to transducers forming part of a microprocessor-based computer and display device 22 having an input keyboard 42. It also employs a capnometer sensor 84 which provides an electrical output representative of the instantaneous percentage of $CO_2$ in the gas passing through the capnometer, on line 86 to the microprocessor-based computer and display device 22.

One side of the capnometer is connected to a respiratory connector mouthpiece 88. One side of the bidirectional volume flow meter 80 is connected to a source of respiratory gases 90 which is preferably ambient air. The system 78 could incorporate humidity and/or temperature sensors like the other embodiments or the computing device 32 could make calculations based on ambient temperature, barometric pressure and humidity to compensate the flow sensor readings.

The passageways interconnecting the flow meter 80 and the capnometer 84 include a partition wall 92 extending from near one end of the flow meter 80 to near one end of capnometer sensor 84. A shorter partition 94 extends parallel to the partition 92 adjacent the capnometer sensor. A switchable partition 96 may be controlled by a signal on line 98 from the computing device 22 to move between the illustrated position in which it extends between the two ends of the partitions 92 and 94 and blocks flow between them, and an alternative position, illustrated in phantom lines as 96a where it unblocks the space between the partitions 92 and 94 and instead blocks the space between one end of the partition 92 and wall 100 of the conduit interconnecting the flow meter 80 and the capnometer 84.

To make a measurement of oxygen consumption, the partition 96 is switched to the position illustrated in FIG. 4, in which it extends between the ends of the partitions 92 and 94, and blocks the passage of gases between them. When the subject inhales through the mouthpiece 88, respiratory gases are drawn from the source 90 through the bidirectional flow meter 80 and through a one-way valve 102, which extends between the partition 94 and the conduit wall 104. Exhalations through the mouthpiece 88 pass through the capnometer 84 and then through a one-way valve 106, which extends between the end of the partition 92 near the capnometer and the wall 100 of the conduit. The exhalations pass out the bi-directional flow meter 80 to the source of respiratory gases 90.

Like the embodiments of FIGS. 1 and 2, the computing device 22, receiving signals from the flow sensor 80 and the capnometer 84, generates the signal $VO_2$ by subtracting the exhalation flow volume, less the volume of $CO_2$ in the exhalation, as calculated by integrating the instantaneous $CO_2$ signal from the capnometer 84 over the exhalation flow signal from the flow sensor 80, from the inhalation volume as measured by the flow meter 80. REE and RQ may be calculated in the same manner as in the previous embodiments.

The system 78 may be used to calculate Cardiac Output in the same manner as the combined oxygen and cardiac output analyzer disclosed in U.S. Pat. No. 5,836,300 also to Mault, and incorporated herein by reference. This implements the nonevasive method of cardiac output measurement using $CO_2$ rebreathing described in an article by Capek and Roy in the *IEEE Transactions in Biomedical Engineering,* Volume 35, pages 653–61, 1988. Essentially, with the partition 96 in the position illustrated in FIG. 4, $VO_2$, $VCO_2$, and end-tidal $CO_2$ (etCO2) are recorded over 3 minutes. The occurrence of the end-tidal time is detected by examining the output of either the flow sensor or the capnometer. The partition 96 is then switched so that the input to valve 106 is blocked. During exhalation, a portion of the exhaled breath is stored in the volume between the partition 92 and the wall 104. When the user inhales, the initial portion of the inhalation constitutes this previously breathed gas and the balance is drawn from the respiratory gas source 90 through the bi-directional volume flow meter 80. During this period, the breath-to-breath $\Delta etCO_2$ and total $VCO_2$ are recorded. The computing device 22 then implements the calculation:

$$C.O. = \frac{\Delta VCO_2}{\Delta etCO_2}$$

where $\Delta VCO_2$ equals the difference in the total volume of exhaled $CO_2$, per breath, during the two recordings and $\Delta etCO_2$ is the change in the end-tidal $CO_2$ content of an exhalation between the first recording and the second recording, with the end-tidal point detected by a zero crossing algorithm in the microprocessor.

In FIG. 4, line 108 provides the output signal from a continuous pulse oximeter 110, preferably of the type attached to a subject's finger, to allow the measurement of Delivered Oxygen ($DO_2$). The measured or estimated hemoglobin value of the subject is entered via keyboard 42 by the operator. The computing device 22 then implements the equation:

$$DO_2 = (C.O.)(SpO_2)(Hgb)(1.36)$$

where $SpO_2$ equals the blood oxygenation as measured by the oximeter 110. As will be recognized by those skilled in the art, the capnometer employed in the preferred embodiment may be substituted with a type of component gas concentration sensing device to produce substantially the same results.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. An indirect calorimeter operative to measure the respiratory oxygen consumption per unit time of a subject, comprising:

a respiratory connector operative to be supported in contact with a subject so as to pass respiratory gases as the subject breathes into said respiratory connector;

a bi-directional flow meter having an ultrasonic flow transducer that bi-directionally transmits and receives ultrasonic signals to said transducer to generate a signal as a function of the volume of gases passing through said flow meter;

a gas concentration sensor operative to generate a signal as a function of an instantaneous carbon dioxide content of gases passing by said gas concentration sensor;

a computing device operative to receive signals from said flow meter and said gas concentration sensor; and conduits interconnecting said respiratory connector, said flow meter and said gas concentration sensor, so that the subject's inhalations and exhalations pass through the flow meter and the subject's exhalations pass over the gas concentration sensor; the computer being operative to receive the signals from said gas concentration sensor and said flow meter to calculate the subject's oxygen consumption.

2. An indirect calorimeter as set forth in claim 1 wherein one ultrasonic transducer is positioned on an upper wall of the bi-directional flow meter, and another ultrasonic transducer is positioned on a lower wall of the bi-directional flow meter.

3. An indirect calorimeter as set forth in claim 1 wherein said flow meter includes an ultrasonic transducer positioned on a side wall of said flow meter at an angle and another ultrasonic transducer positioned on the side wall opposing said first transducer at an angle, so that ultrasonic pulses from said transducers are transmitted at an angle to the gas flow direction.

4. An indirect calorimeter as set forth in claim 1 wherein said ultrasonic transducer includes a plurality of microscopic transducers arranged in an array.

5. An indirect calorimeter as set forth in claim 4 wherein said microscopic transducers measure temperature, pressure and humidity, for correcting the gas flow rate due to the effects of temperature, pressure or humidity.

6. An indirect calorimeter as set forth in claim 1 wherein said gas concentration sensor is an infrared absorption sensor.

7. An indirect calorimeter as set forth in claim 1 wherein said gas concentration sensor is a capnometer.

8. An indirect calorimeter as in claim 1 wherein said gas concentration sensor is a fluorescence based oxygen sensor.

9. An indirect calorimeter as in claim 1 wherein said gas concentration sensor is a combined infrared absorption sensor for measuring the concentration of carbon dioxide and a fluorescent quenching sensor for measuring the concentration of oxygen.

10. An indirect calorimeter operative to measure the respiratory oxygen consumption per unit time of a subject, comprising:

a source of respiratory gases;

a respiratory connector operative to be supported in contact with the subject so as to pass respiratory gases as the subject breathes into said respiratory connector;

a bi-directional flow meter having ultrasonic transducers, wherein said transducers generate a signal as a function of the volume of the gases passing through the flow meter during inhalation and exhalation;

an infrared (IR) absorption sensor, wherein said IR sensor operatively generates a signal as a function of the instantaneous $CO_2$ content of the gases passing over said IR sensor;

a florescence quench sensor, wherein said quench sensor operatively generates a signal as a function of the instantaneous $O_2$ content of the gases passed over said quench sensor;

conduits interconnecting said source of respiratory gases, said respiratory connector, said flow meter, said IR sensor, and said quench sensor, upon the subject inhaling, to cause respiratory gas from said source to pass through said flow meter to the respiratory connection, and upon the subject exhaling to pass the exhaled gas by the IR sensor, the quench sensor and through the flow meter; and a means for receiving the resultant signals from said flow meter, said IR sensor and said quench sensor for determining a volume of $CO_2$ exhaled by the subject over a period of time.

11. An indirect calorimeter as set forth in claim 10, wherein the volume of $CO_2$ exhaled is determined from the integral of the product of the instantaneous flow meter signal by the IR sensor signal over the period.

12. An indirect calorimeter as set forth in claim 11, wherein the oxygen consumption is determined from the integral volume of gases inhaled over the period less the volume gases exhaled over the period multiplied by the quench sensor signals.

13. An indirect calorimeter as set forth in claim 10 wherein one ultrasonic transducer is positioned on an upper wall of the bi-directional flow meter, and another ultrasonic transducer is positioned on a lower wall of the bi-directional flow meter.

14. An indirect calorimeter as set forth in claim 10 wherein said flow meter includes an ultrasonic transducer positioned on a side wall of said flow meter at an angle and another ultrasonic transducer positioned on the side wall opposing said first transducer at an angle, so that ultrasonic pulses from said transducers are transmitted at an angle to the gas flow direction.

15. An indirect calorimeter operative to measure the respiratory oxygen consumption per unit time of a subject, comprising:
- a respiratory connector operative to be supported in contact with a subject so as to pass respiratory gases as the subject breathes into said respiratory connector;
- a bi-directional flow meter having an ultrasonic flow transducer positioned on an upper wall of the bi-directional flow meter, and another ultrasonic flow transducer is positioned on a lower wall of the bi-directional flow meter, that bi-directionally transmit and receive ultrasonic signals between said ultrasonic flow transducer to generate a signal as a function of the volume of gases passing through said flow meter;
- a gas concentration sensor operative to generate a signal as a function of an instantaneous carbon dioxide content of gases passing by said gas concentration sensor;
- a computing device operative to receive signals from said flow meter and said gas concentration sensor; and
- conduits interconnecting said respiratory connector, said flow meter and said gas concentration sensor, so that the subject's inhalations and exhalations pass through the flow meter and the subject's exhalations pass over the gas concentration sensor; the computer being operative to receive the signals from said gas concentration sensor and said flow meter to calculate the subject's oxygen consumption.

16. An indirect calorimeter as set forth in claim 15 wherein said flow meter includes an ultrasonic transducer positioned on a side wall of said flow meter at an angle and another ultrasonic transducer positioned on the side wall opposing said first transducer at an angle, so that ultrasonic pulses from said transducers are transmitted at an angle to the gas flow direction.

17. An indirect calorimeter as set forth in claim 15 wherein said ultrasonic transducer includes a plurality of microscopic transducers arranged in an array.

18. An indirect calorimeter as set forth in claim 17 wherein said microscopic transducers measure temperature, pressure and humidity, for correcting the gas flow rate due to the effects of temperature, pressure or humidity.

19. An indirect calorimeter as set forth in claim 15 wherein said gas concentration sensor is an infrared absorption sensor.

20. An indirect calorimeter as set forth in claim 15 wherein said gas concentration sensor is a capnometer.

21. An indirect calorimeter as in claim 15 wherein said gas concentration sensor is a fluorescence based oxygen sensor.

22. An indirect calorimeter as in claim 15 wherein said gas concentration sensor is a combined infrared absorption sensor for measuring the concentration of carbon dioxide and a fluorescent quenching sensor for measuring the concentration of oxygen.

* * * * *

UNITED STATES PATENT AND TRADEMARK OFFICE
CERTIFICATE OF CORRECTION

PATENT NO. : 6,572,561 B2
DATED : June 3, 2003
INVENTOR(S) : James R. Mault

It is certified that error appears in the above-identified patent and that said Letters Patent is hereby corrected as shown below:

<u>Title page,</u>
Item [56], References Cited, insert heading -- FOREIGN PUBLICATIONS --; and under "FOREIGN PUBLICATIONS" insert -- wo oo/1300, 8/99 --.
Insert heading -- OTHER PUBLICATIONS --; and under "OTHER PUBLICATIONS" insert -- IEEE Transactions On Biomedical Engineering, vol. 35, No. 9, September 1988, pp. 653-659, Capek et al., "Noninvasive Measurement of Cardia Output Using Partial CO2 Rebreathing." --

Signed and Sealed this

First Day of June, 2004

JON W. DUDAS
*Acting Director of the United States Patent and Trademark Office*